(12) United States Patent
Ivansson et al.

(10) Patent No.: US 9,983,203 B2
(45) Date of Patent: May 29, 2018

(54) METHOD FOR PROTEIN ANALYSIS (71) Applicant: GE Healthcare Bio-Sciences AB, Uppsala (SE)

(72) Inventors: Daniel Ivansson, Uppsala (SE); Camilla Estmer Nilsson, Uppsala (SE); Therese Graner, Uppsala (SE); Johan Ohman, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 9 days.

(21) Appl. No.: 15/108,505

(22) PCT Filed: Feb. 12, 2015

(86) PCT No.: PCT/SE2015/050169
§ 371 (c)(1),
(2) Date: Jun. 27, 2016

(87) PCT Pub. No.: WO2015/122835
PCT Pub. Date: Aug. 20, 2015

(65) Prior Publication Data
US 2016/0320377 A1    Nov. 3, 2016

(30) Foreign Application Priority Data

Feb. 13, 2014  (SE) .................................... 1450168

(51) Int. Cl.
| G01N 33/53  | (2006.01) |
| C12Q 1/68   | (2018.01) |
| G01N 33/543 | (2006.01) |
| G01N 33/68  | (2006.01) |
| C07H 21/04  | (2006.01) |
| G01N 33/48  | (2006.01) |
| G01N 33/483 | (2006.01) |
| C40B 30/04  | (2006.01) |

(52) U.S. Cl.
CPC ..... G01N 33/54333 (2013.01); C12Q 1/6804 (2013.01); G01N 33/5308 (2013.01); G01N 33/54306 (2013.01); G01N 33/54353 (2013.01); G01N 33/6803 (2013.01); *G01N 2333/79* (2013.01); *G01N 2458/10* (2013.01)

(58) Field of Classification Search
None
See application file for complete search history.

(56) References Cited

FOREIGN PATENT DOCUMENTS

| CN | 102586450 A    | 7/2012  |
| WO | 2012/057689 A1 | 5/2012  |
| WO | 2012/152942 A1 | 11/2012 |

OTHER PUBLICATIONS

Lundberg et al., "Homogenous antibody-based proximity extension assays provide sensitive and specific detection of low-abundant proteins in human blood", Nucleic Acids Research, Jun. 6, 2011, vol. 39, No. 15, e102, 8 pages.
Gold et al., "Aptamer-Based Multiplexed Proteomic Technology for Biomarker Discovery", PLOS ONE, Dec. 2010, vol. 5, e15004, 17 pages.
International Search Report and Written Opinion regarding International Application No. PCT/SE2015/050169, dated Apr. 29, 2015, 8 pages.
Michael A Gillette & Steven A Carr, 'Quantitative analysis of peptides and proteins in biomedicine by targeted mass spectrometry', vol. 10, No. 1, Jan. 2013, Nature Methods, 7 pages.
I. Weibrecht et al., 'Proximity ligation assays: a recent addition to the proteomics toolbox', Expert Reviews,Proteomics 7(3), 2010, pp. 401-409.
Green, N.M.; 'A spectrophotometric assay for avidin and biotin based on binding of dyes by avidin,' Biochem. J., 1965, 94, 23c-24c, 2 pages.
J. Göransson et al., 'Rapid Identification of Bio-Molecules Applied for Detection of Biosecurity Agents Using Rolling Circle Amplification', PlosOne, Feb. 2012, vol. 7, Issue 2, 9 pages.
T. Zardan Gomez de la Torre et al., 'Detection of rolling circle amplified DNA molecules using probe-tagged magnetic nanobeads in a portable AC susceptometer', Biosensors and Bioelectronics, 29 (2011), pp. 195-199.
S. Darmanis et al., 'ProteinSeq: High-Performance Proteomic Analyses by Proximity Ligation and Next Generation Sequencing,' PlosOne, Sep. 2011, vol. 6, Issue 9, 10 pages.
Y.Liu et al., 'Western blotting via proximity ligation for high performance protein analysis', Molecular and Cellular Proteomics, Nov. 2011, 10.11, 9 pages.
Users manual Proseek® Assay Development kit, Olink Bioscience, 2011, 28 pages.
Instructions for ExcelGel SDS, gradient 8-18, GE Healthcare 80-1310-00, 2006, 20 pages.
Instruction manual NHS Mag Sepharose™ 28-9537-64, GE Healthcare AB, Nov. 2010, 12 pages.

*Primary Examiner* — Nancy J Leith
(74) *Attorney, Agent, or Firm* — Eversheds Sutherland (US) LLP (57) ABSTRACT

Provided are methods for protein analysis in which proteins to be analyzed are displayed on a population of discrete and dispersible structures, such as beads or other particles, for subsequent affinity reactions and analysis/detection. The proteins to be analyzed may be provided as denatured protein samples in the presence of a denaturing agent.

23 Claims, 8 Drawing Sheets

METHOD FOR PROTEIN ANALYSIS

CROSS-REFERENCE TO RELATED APPLICATIONS

This application is a filing under 35 U.S.C. 371 of international application number PCT/SE2015/050169, filed Feb. 12, 2015, which claims priority to SE application number 1450168-8, filed Feb. 13, 2014, the entire disclosures of each of which are hereby incorporated by reference.

FIELD OF THE INVENTION

The present invention relates to a method for protein analysis. More closely the invention relates to a method for protein analysis in which the proteins to be analyzed are displayed on a population of discrete and dispersible structures, such as beads or other particles, for subsequent affinity reactions and analysis/detection.

BACKGROUND

Even though the number of genes in the human genome is much smaller than initially thought (around 20 000), the complexity and heterogeneity of human biology in health and disease has proven overwhelming. Improved knowledge and methods to define different phenotypic states are critically sought. This is driven both by basic research with the emerging Systems Biology dogma and more importantly by the realization that healthcare needs to be more personalized leading to needs to adjust/improve both drug development and disease management by development and use of biomarkers as tools for disease characterization, patient stratification and evaluation of efficacy and potential adverse effects of a treatment.

Proteins as a class have great promise as a source of biomarkers since they are the main functional actors in biological systems and define the phenotype. Not all medical indications have a direct genetic component and neither genome data nor mRNA expression data are fully predictive of protein amounts or protein states and variants.

Tissue based protein biomarkers are likely needed for detailed disease characterization (such as pathway/drug escape monitoring during cancer treatment) and patient stratification/detailed diagnosis due to potential distortion and the inherent dilution of information during leakage of proteins into circulation. In addition the applicability of "tissue based biomarkers" is increasing rapidly with the exploration of diagnostic information in liquid biopsies such as circulating tumor cells, exosomes and other micro-vesicles. Currently there are three main groups of methodologies specifically suited for general analysis of proteins directly in tissue/cells/micro-vesicles or extracted from tissue/cells/micro-vesicles:

In Immunohistochemistry (IHC), formalin-treated tissue sections are interrogated with labeled antibodies (and other stains for morphology) and read-out is performed by the use of advanced microscopes. This is potentially the most information-rich method since proteins are measured in their biological context and heterogeneity between cell types can be assessed. However, it has limited ability to detect protein isoforms, limited multiplexing capabilities and you need an expensive microscope. In addition, sample pre-treatment for antigen retrieval can be quite complex and generally need tailoring for different sets of targets.

In Western Blotting (WB), proteins from tissue are extracted and denatured before separated using i.e. sodium dodecyl sulfate polyacrylamide gel electrophoresis (SDS-PAGE), transferred to a porous membrane and interrogated with labeled antibodies (chemiluminiscence or fluorescence). Read-out is performed using either a scanner or a CCD-based system. However, WB has severe limitations for more advanced applications such as for protein biomarkers. It has limited quantification capability, limited sensitivity and dynamic range, limited abilities to distinguish isoforms and very limited multiplexing capabilities. The workflow is also relatively complicated and difficult to scale up for high throughput.

In MRM-MS/MS based methods, proteins are extracted and denatured before being digested into peptides [1]. Proteins are then quantified via their proteotypic peptides using a special form of MS read-out (MRM or SRM). However it has several important challenges: (a) low sensitivity without advanced pre-fractionation, (b) quantification variability, (c) long time to achieve results and relatively low throughput, (d) general detection of protein isoforms will likely be a challenge for many years to come.

Perhaps most important is the fact that for all of the above methodologies it will be difficult to implement standardized and automated solutions in a low cost and easy to use platform that can promote wide adoption and measurements of very large number of samples. Hence, in summary there is still a need for improved protein analytics for analyzing clinical samples of tissue, cells or micro-vesicles.

Affinity based proximity assay technology offers a novel and highly versatile toolbox for analysis of proteins and protein features. It is based on affinity binders coupled to oligonucleotides and the conditional creation of target specific nucleic acid molecules as a result of a combination of proximal binding of two or more affinity binders carrying different oligonucleotides and the action of nucleic acid processing enzymes. Different implementations such as Proximity Ligation Assays (PLA) [2], Proximity Extension Assays (PEA) [3], Rolling Circle Product PLA (RCP-PLA) [4] and Unfolding Proximity Probe assays [5] for measurements on proteins in solution have been described. Nucleic acid signals created as a result of proximal reactions can be detected and quantified in a number of ways including Q-PCR [3], digital detection of RCPs using fluorescence read-out [4], detection of RCPs using magnetic detection [6] and digital detection using third generation sequencing [7]. Since information about which set of affinity binders that has bound in proximity is present in the generated signal, the technology is uniquely suited to avoid the fundamental issue of cross-reactivity which stops any direct sandwich immunoassay implementation from enabling accurate multiplexed results in complex solution based protein samples. The increased specificity also opens up for increased sensitivity and ability for detection of specific isoforms and protein complexes in solution.

A special implementation of the technology (In-situ PLA [2]) has previously also been developed [8-9] to allow improved detection capabilities for proteins in Western Blotting workflows. Increased abilities include improved specificity, ability to detect isoforms such as phosphorylation directly using one signal and improved sensitivity.

SOMAmer affinity assay technology using a specifically designed category of nucleic acid aptamers allowing dual specificity building events to be incorporated using a single binder molecule have recently been developed by Larry Gold et al. [10]. This development has allowed a route to significantly reduce cross-reactivity issues for multiplexed assays in complex protein samples in solution while still keeping the specificity of a single analyte sandwich assay.

An assay simultaneously detecting close to a thousand analytes has been reported based on this technology [10].

A major concern when analyzing proteins extracted from sources such as tissue biopsies, cells from culture, primary cells such as circulating tumor cells and micro-vesicles such as exosomes is being able to maintain the in-vivo distribution of protein amounts and modification states in the sample brought forward to analysis. Degradation or modification of proteins through altered enzymatic activity post sample acquisition is one of the challenges. Protein degradation or modification can be caused either by changes in the physiological state of the collected cells due to perturbations of the cells natural environment and/or new enzymatic activity coming into contact with targeted proteins during the extraction procedure. Another challenge is to achieve complete and reproducible extraction and solubilization of all the proteins present in the original sample. To control the above issues it is generally necessary to achieve rapid inactivation of enzymatic activity through protein denaturation coupled with the use of efficient solubilizing agents to extract proteins from the in-vivo architecture and avoid precipitation of denatured proteins. A preferred strategy for stringent sample processing is the use of a combination of heat and SDS as a solubilizing and denaturing agent. With the exception of some MS based workflows and WB, available protein analysis technologies are generally not compatible with such extraction strategies.

SUMMARY OF THE INVENTION

As an attempt to comply with the above protein extraction considerations and at the same time resolve many of the challenges and shortcomings previously described for current state-of-the-art tissue protein analysis methods a new protein analysis concept termed "The Blotting Beads Concept" was conceived and developed by the present inventors. It utilizes dispersible protein binding structures to display and isolate proteins from denaturing conditions before applying powerful affinity based reactions. One of the key aspects of the concept is that it enables application of powerful protein assay technologies, such as the ones described above, generally used for non-denatured samples of soluble proteins also for samples prepared using stringent denaturing conditions and hence allows assay performance previously not possible for these type of samples.

Protein analysis workflows utilizing protein binding to dispersible particles as unit operations are common in the prior art. For example as a clean-up, enrichment or pre-fractionation step prior to MS analysis or as a protein specific capture step in affinity assay implementations. However, to our best knowledge no example is available in the prior art where particles containing protein binding ligands with broad specificity have been used to display proteins from denaturing conditions and being followed by affinity assay reactions capable of detecting multiple proteins simultaneously.

Thus the present invention relates to a method for protein analysis comprising providing a denatured protein sample in the presence of a denaturing agent, the method comprising the following steps;
a) contacting said protein sample with a population of discrete and dispersible protein-binding structures to capture a plurality of different proteins on said structures,
b) removal of denaturing agent to display protein- and protein-feature specific epitopes from said sample on said structures;
c) performing affinity probing targeted to a sub-group of said protein or protein feature specific epitopes requiring two or more specificity building events per targeted protein or protein feature generating a target specific nucleic acid molecule or sequence for each of the targeted proteins or protein-features;
d) liberating said protein- or protein-feature specific nucleic acid sequences or their complements from said structures;
e) optionally amplifying said nucleic acid sequences;
f) analysing the generated nucleic acid molecules by a quantitative and sequence specific nucleic acid detection method; and
g) determining therefrom the quantity or presence of targeted proteins or protein features in said sample.

Preferably the protein binding structures are selected from the groups of microparticles, nanoparticles, nanofibers or combinations thereof. Most preferably the protein binding structures are selected from porous or non-porous structures of natural, such as polysaccharides or synthetic polymers, such as polystyrene, ceramic structures, metallic structures or combinations thereof.

In a preferred embodiment the protein binding structure is an agarose bead, provided with paramagnetic particles, preferably Mag Sepharose™.

The discrete protein binding structures in the population may all have identical binding specificities or may collectively have multiple binding specificities. This can either be achieved by having multiple binding ligands on each discrete protein binding structure, by combining sub-populations of protein binding structures were each sub-population carries different protein binding ligands or a combination thereof.

According to the method of the invention multiple proteins or protein features may be targeted by affinity probing and nucleic acid detection to generate a multiplex determination of quantity or presence of said proteins or protein features simultaneously.

The proteins in said protein sample may be conjugated to a hapten and said protein binding structures then contain an affinity ligand directed against the hapten. Preferably the hapten is biotin and the affinity ligand is streptavidin or avidin. In a preferred embodiment unreacted excess hapten reagents are reduced or removed following conjugation and prior to contacting the sample with protein binding structures.

In an alternative embodiment said protein binding structures are chemically activated and contacting said sample results in covalent coupling of proteins to the structures. Preferably said protein binding structures are NHS activated.

The protein denaturing agent may be selected from the group consisting of sodium dodecyl sulfate (SDS), lithium dodecyl sulfate (LDS), Urea, Thio-Urea or Guanidine-HCl. Optionally the sample has been heated to above 80° C., preferably 95° C., in the presence of a denaturing agent from said group. SDS is the preferred denaturing agent.

In a further embodiment, the SDS concentration in said sample is reduced to a range of 0.1-0.3% prior to step a) contacting the sample with protein binding structures, wherein the method further comprising the steps of:
(i) contacting the denatured protein sample with porous lid beads designed with a hydrophilic surface layer allowing only low molecular weight molecules to enter the inner pore volume which is modified with octylamine ligands having affinity for SDS;
(ii) allowing SDS to accumulate within the lid beads for a defined time period; and (iii) removing the lid beads from the sample A great advantage of the method according to the invention is that following capture on the protein binding structures in step a), the population of structures may be isolated and re-suspended in a stability promoting storage solution. Before steps b) and c) the structures are isolated from the storage solution and re-suspended in a buffer suitable for affinity probing (step c). This is not possible with current affinity probing techniques.

The affinity probing may comprise the following steps:
(I) contacting the structures with captured proteins with one or multiple aptamers each having been selected for having high affinity and slow-off rate for a single protein- or protein feature specific epitope
(ii) isolating the structures after having allowed time for protein-aptamer binding
(iii) re-suspending the structures in a solution containing poly-anions to promote a differential release of non-specifically bound aptamers enabled by the slow off-rate of the specific interaction
(iv) Isolating the structures
(v) re-suspending the structures in a solution and treating them to promote elution of the aptamers still bound after the poly-anion treatment Alternatively the affinity probing is based on affinity binders coupled to oligonucleotides and the conditional creation of target specific nucleic acid molecules as a result of a combination of proximal binding of two or more affinity binders carrying different oligonucleotides to the same protein or protein-feature target and the action of nucleic acid processing enzymes added during the probing. Proximity extension reactions or proximity ligation reactions may be used, which is explained more closely in the detailed section of the invention.

Any suitable method may be used for nucleic acid detection, such as quantitative PCR, an oligonucleotide array or any sequencing procedure allowing counting individual sequence readings.

The detection may also comprise the steps of:
(i) using rolling circle amplification reactions to create DNA-spheres consisting of condensed linear repeats of protein or protein feature specific nucleic acid molecules;
(ii) hybridizing the DNA spheres with labeled detection oligonucleotides specific for each protein or protein feature specific DNA sphere; and
(iii) detecting a signal proportional to the number of DNA spheres present.

The DNA spheres may be fluorescently labeled and digitally counted in a flow system or the DNA spheres are labeled by magnetic nanoparticles and detected using magnetorelaxometry.

DETAILED DESCRIPTION OF THE INVENTION

Figure 1A:
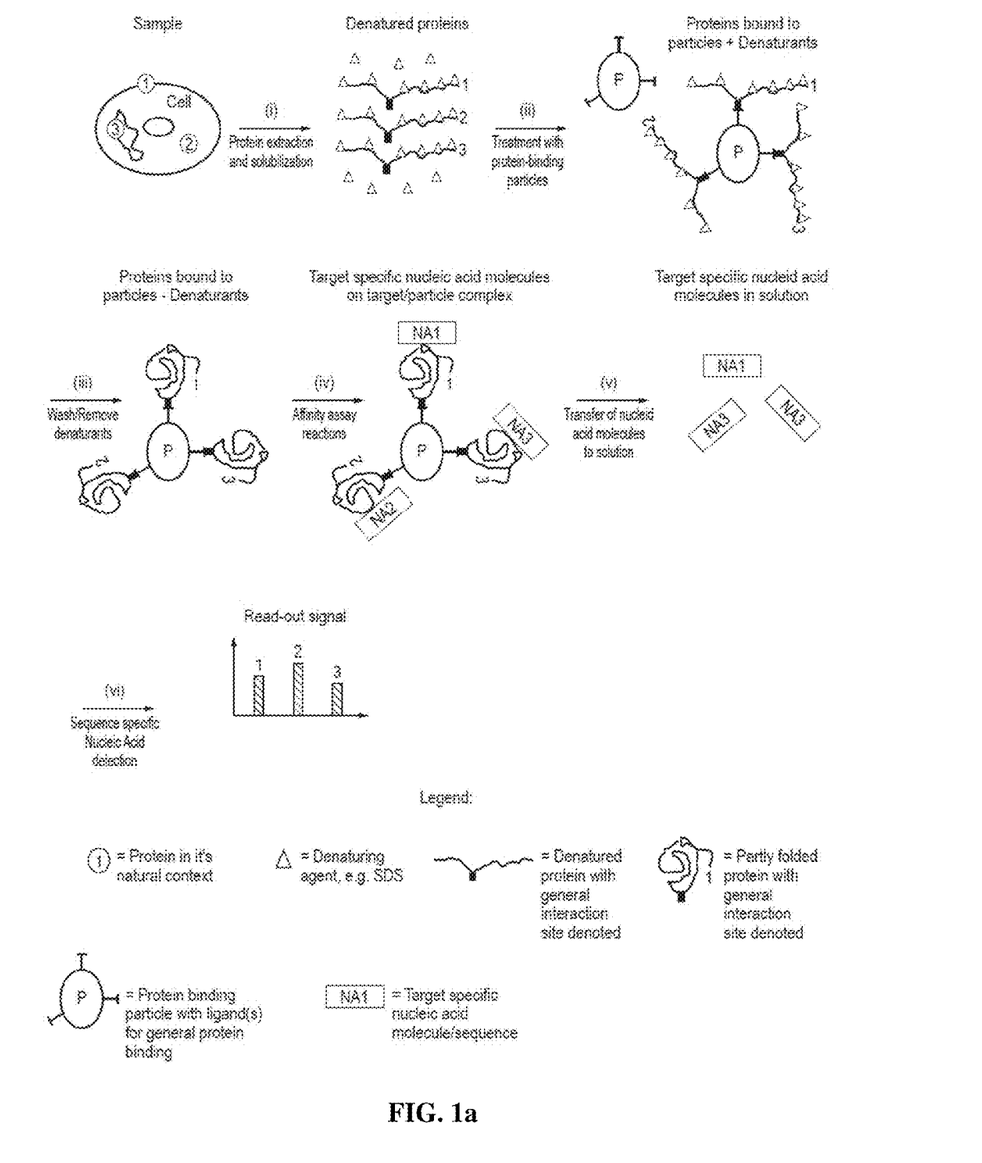
FIG. 1a describes an overview of the general implementation of the novel protein analysis concept including affinity binding of proteins to microparticles/beads, FIGS. 1b and 1c describe further details about steps (iv) and (v) in FIG. 1a around implementations of the affinity reactions steps being part of the analysis workflow.

The general concept is summarized in FIG. 1a. Protein samples from various sample sources (Tissue biopsies, cultured cells, primary cells, exosomes and other microvesicles, bio-fluids, protein standards etc.) are prepared using denaturing conditions and provided in the presence of denaturing agents to ensure efficient extraction and protein solubility of proteins from various compartments in the sample (e.g. plasma membrane proteins, cytosolic protein or proteins from organelles). Samples are then treated with a population of discrete and dispersible protein-binding structures. These structures can be microparticles, nanoparticles, nanofibers or combinations thereof. However, they are hereafter exemplified by referring to protein binding particles. The protein-binding particles have binding ligands and binding mechanisms compatible with the presence of denaturing agents and may contain single or multiple specificities designed to collectively bind a comprehensive set of the proteins present in the sample. Hence, multiple different proteins will be bound to each individual protein binding particle. Following capture of proteins on the particles the particles/particle-bound proteins are treated using conditions to promote removal of denaturing agents, resulting in the display of protein- and protein feature specific epitopes. During this step, the binding of proteins to the particles serves to prevent protein precipitation and aggregation via isolation/immobilization of individual protein molecules on particles that can be brought in and out of dispersion.

A multitude of different specific implementations of the general concept is possible and a few of these are described here for illustration. In one preferred implementation, SDS is used as a solubilizing/denaturing agent prior to treatment with protein-binding particles. In one preferred implementation of the protein binding step, proteins are first covalently modified to contain a hapten having a stable, high-affinity interaction partner that is immobilized on a protein binding particle. The hapten-modified protein sample is then treated using the particles containing the interaction partner. A specific implementation is the use of biotin as a hapten and streptavidin as an interaction partner. In a particularly preferred implementation of the protein binding step, activated protein binding particles enabling direct covalent binding with broad protein specificity are used. A specific implementation is the use of NHS-activated protein binding particles.

Next, affinity probing reactions capable of generating protein- or protein-feature specific nucleic acid signals dependent on two or more specificity building events in parallel (See FIG. 1b) or in series (See FIG. 1c) are performed on the particles. Affinity assay reactions used are generally of two main categories: Proximity assays or aptamer assays using slow off-rate aptamers coupled with a kinetic challenge (See FIG. 1b or 1c and below for more details).

Figure 1B:
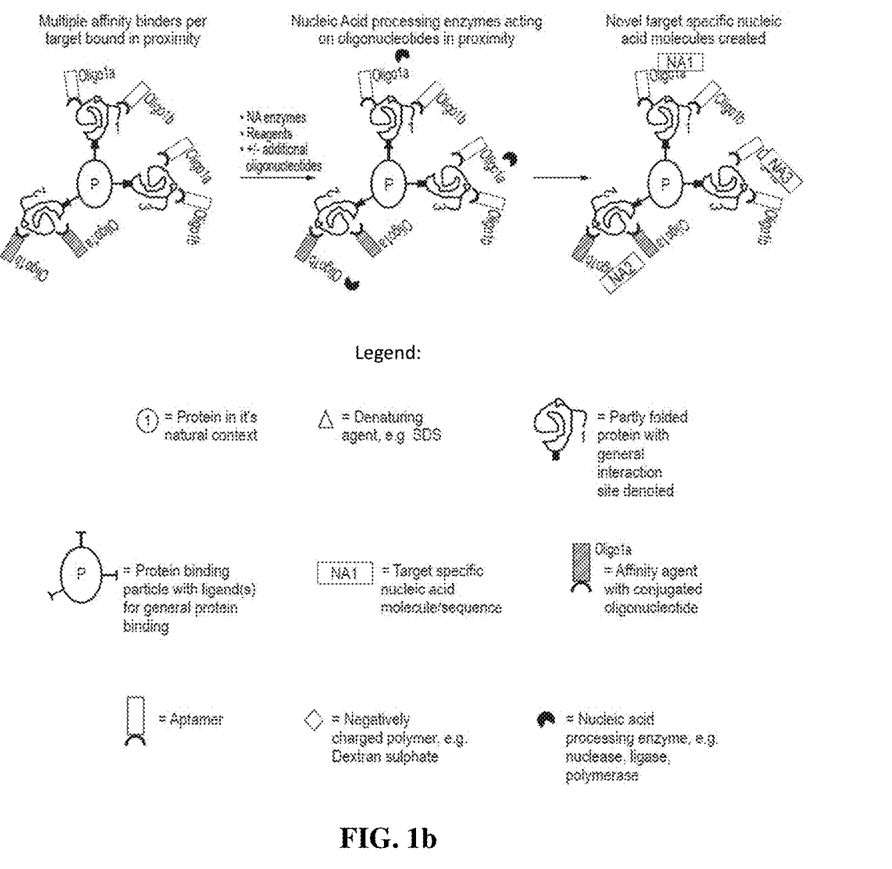

In a most preferred implementation of the affinity probing steps, proximity assays based on affinity binders coupled to oligonucleotides and the conditional creation of target specific nucleic acid molecules as a result of a combination of proximal binding of two or more affinity binders carrying different oligonucleotides and the action of nucleic acid processing enzymes are used. FIG. 1b exemplifies this approach using two affinity binders. A mixture of affinity binders are allowed to react with proteins bound to particles. For each targeted protein or protein feature, two populations of binders directed against different epitopes of the target and conjugated to epitope-coded oligonucleotides are present. Following binding, nucleic acid processing enzymes such as ligases, nucleases or polymerases are added together with reagents and potentially additional oligonucleotides. This will result in the creation of new nucleic acid sequences with a target specific combination of epitope-coded sequences. The oligonucleotide sets and reaction conditions are designed in such a way that creation of new nucleic acid sequences in solution is highly unlikely and highly enhanced by the increased local concentration following proximal binding. The created target specific nucleic acid molecules or their complement can then be transferred to solution by elution promoted by a combination of buffer change/heat or by an additional enzymatic step using e.g. a nuclease or a polymerase. Unspecific binding of two or more binders corresponding to the same protein is highly unlikely and signals from combinations of two unspecifically bound binders corresponding to two different proteins are not detected due to the sequence specific detection step. This implementation enables modular specificity, detection of specific protein isoforms and the ability to reach high specificity using a polyclonal antibody preparation split in two or more aliquots and conjugated to individual oligonucleotides.

Figure 1C:
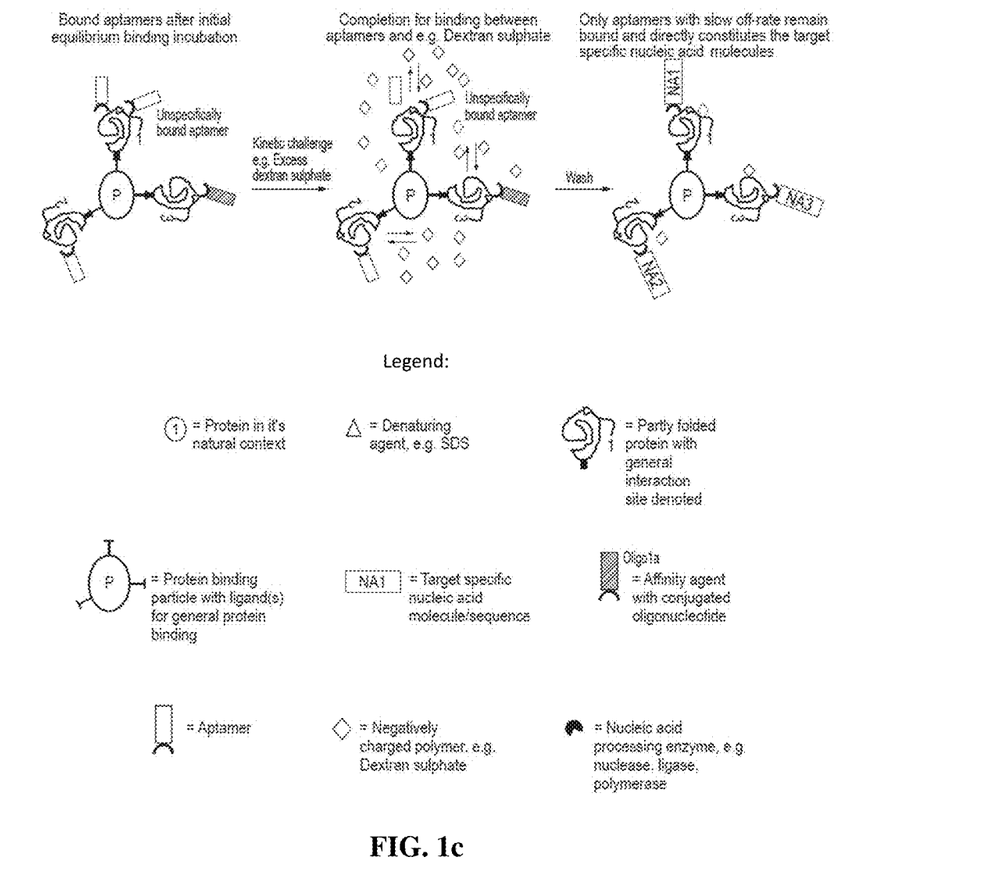

In a preferred implementation of the affinity probing steps, high affinity and slow off-rate aptamers targeting single protein or protein-feature specific epitopes are used in a specifically designed assay implementation (See FIG. 1c). One or multiple aptamer binder variants are first allowed to react with the proteins bound to the particles. The specificity of the equilibrium binding constitutes the first specificity building step. Particles are then isolated and washed before they are re-suspended and incubated in a solution containing an excess of a poly-anion such as dextran sulphate. This kinetic challenge for the bound aptamers constitutes a second specificity building step. Non-specifically bound aptamers will have a faster off-rate and re-binding will be significantly reduced since the main mechanism for non-specific binding of aptamers is electrostatic and this route is efficiently reduced by competition with excess poly-anion. Following the kinetic challenge, the particles are once again isolated and washed. The aptamers that are still bound directly constitutes the protein or protein-feature specific DNA sequences used for detection. However, before detection particles are re-suspended in a solution promoting elution of the aptamers and optionally treated to further promote elution (e.g. via heat).

Finally, created protein- or protein-feature specific nucleic acid molecules or their complements are rendered free from the particles and quantified and/or detected using sequence specific nucleic acid detection methods. Due to the compatibility with affinity assay designs enabling two or more specificity building events, high-specificity detection of targeted proteins or protein features can be achieved despite the non-specific nature of the first capture step and without the molecular weight information present for western blot and similar protein detection implementations.

On-particle detection via for example fluorescence readout is used in multiple technologies such as in protein bead arrays which allows multiplexed detection of protein via the use of multiple bead sets each having a unique fluorescent barcode and a capture ligand targeting a single protein. However, multiplexed detection of proteins bound to particles via an initial non-specific capture step is prohibited from using the bead-array approach since all targeted proteins could be present on all individual bead sets. Via the use of affinity assays generating barcoded nucleic acid sequences that can be rendered free from the particles, sequence specific nucleic acid detection methods can be used and hence giving a potential for very high multiplexing levels. Compatibility with solution based nucleic acid detection technologies also enables the use of sequence specific signal amplification technologies giving potential for exceptional detection sensitivities.

Figure 2A:
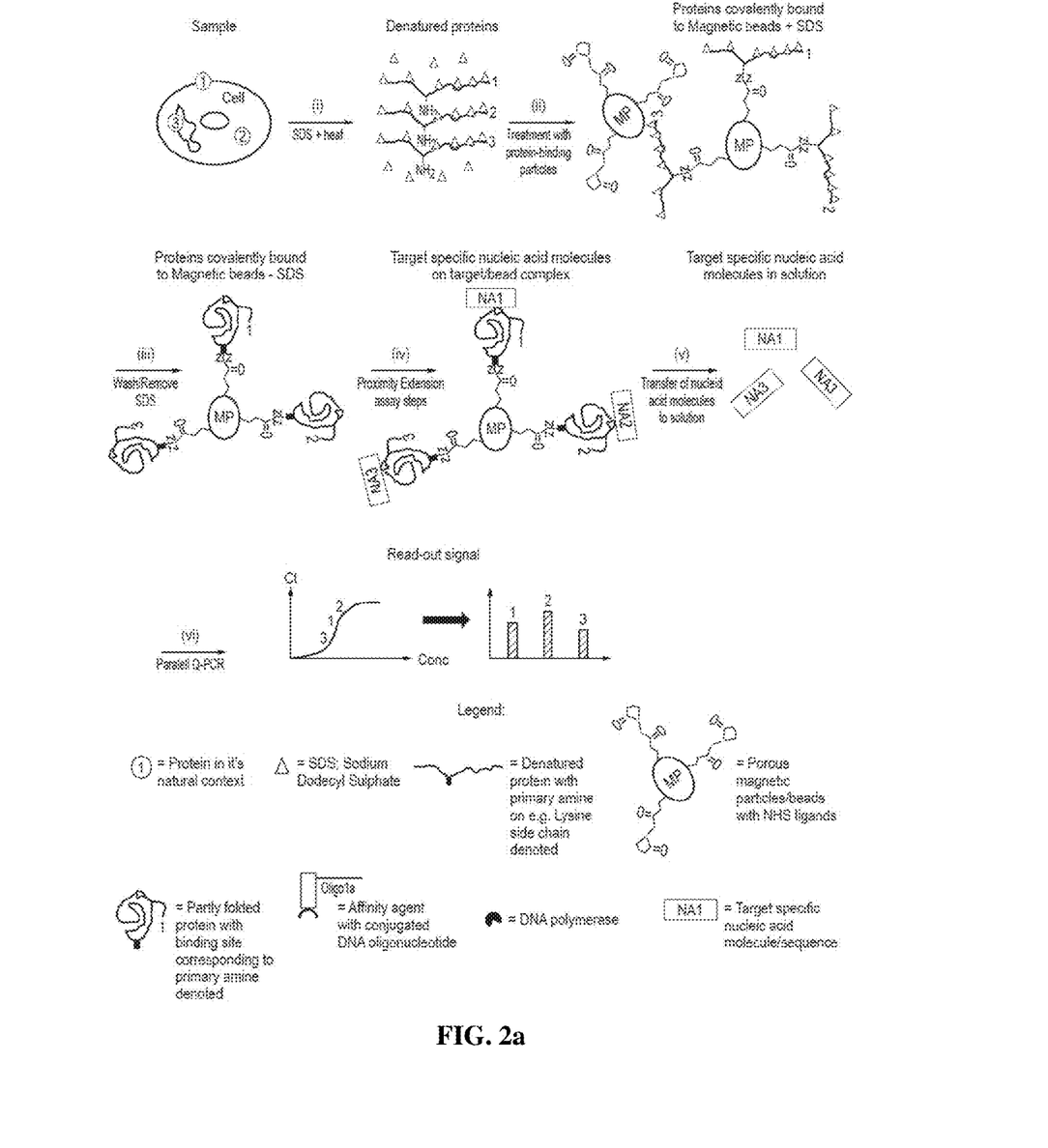
FIG. 2a describes a general overview of a preferred specific implementation of the concept which includes covalent coupling of proteins to NHS activated paramagnetic beads followed by detection using proximity extension assays (PEA) with Q-PCR read-out, FIG. 2b describes further details of the PEA steps.
Figure 2B:
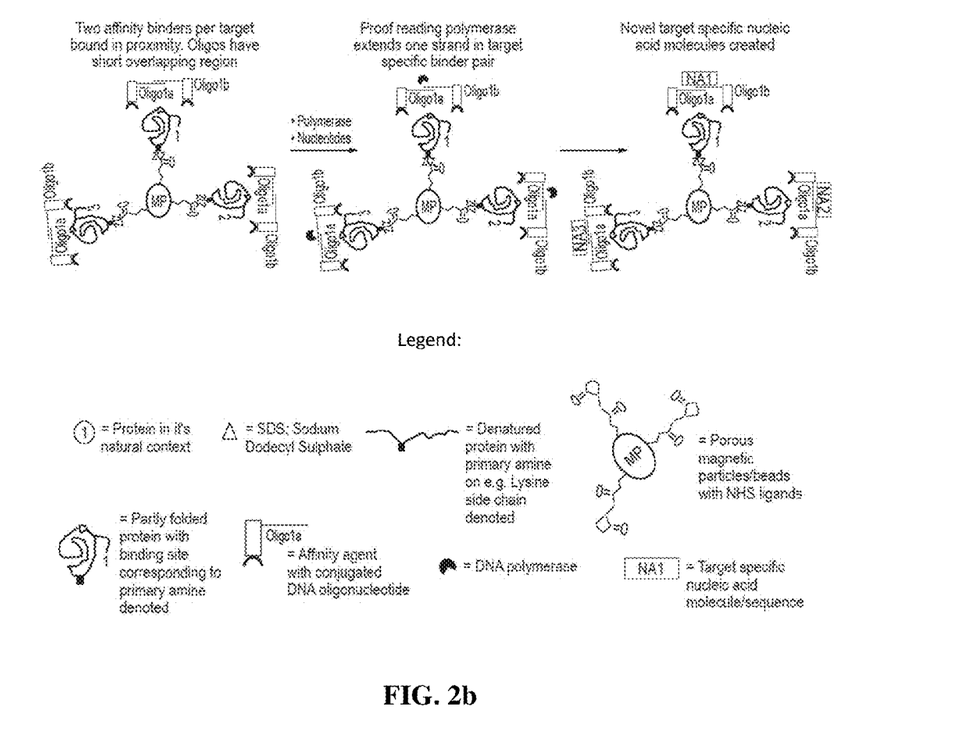

In a preferred implementation of the full workflow (See FIG. 2), SDS is present as a solubilizing denaturing agent. Prior to treatment with protein binding particles an optional SDS dilution step or SDS reduction step using SDS scavenger beads/lid beads can be introduced. SDS adjusted samples are then treated using NHS activated porous paramagnetic beads to covalently bind proteins present in the sample via primary amines that are not masked by bound SDS. Due to the covalent binding of proteins harsh washing steps coupled with isolation of protein binding particles can be introduced to remove most SDS, including the fraction bound proteins, to allow partial folding and display of protein or protein feature specific epitopes. A specific proximity assay implementation called proximity extension assay (See FIG. 2b) is then used. Binders directed against a specific protein target have been conjugated to one of two different oligonucleotides, each pair being unique for one target. Further, each oligonucleotide pair is designed to have a short stretch of sequence complementary. In solution hybridization is rare and unstable due to the low binding affinity. However, as a mixture of affinity binders are allowed to interact with proteins bound to particles, pairs of affinity binders will bind in proximity to their corresponding targets. This enables formation of a stable double-stranded region between the complementary sequences in each oligonucleotide pair. An optional wash step can be introduced to remove unbound affinity probes. Next nucleotides and a polymerase with proof reading exonuclease activity are added to the solution with protein binding beads. As a result, the double stranded region formed between two binder probes bound in proximity is extended so that a new nucleic acid sequence is created. Transiently double stranded regions formed in solution are generally degraded by the exonuclease activity of the polymerase, hence keeping background signal generation low. The newly created nucleic acid molecules can then be released from the beads by e.g. a heat incubation step. Released nucleic acid sequences are finally detected and quantified using parallel Q-PCR reactions.

Compared to In-situ PLA applied to Western Blotting [8-9] the current invention offers multiple potential improvements. In WB-PLA, the signal generated following probing with two or more affinity binders is localized and need to be read-out using fluorescence or chemo-luminescence. Hence, only a limited multiplexing capability, dependent on non-overlapping flourophores, can be readily implemented. Further, without tailoring the equipment and workflow for each new protein to detect, the full blotting membrane needs to be probed making the assays expensive due to large probing volumes. Handling of electrophoresis, transfer and membrane probing is also problematic to automate and even more so in a fashion enabling scalable throughput. By moving the display of proteins from a membrane to particles that can be brought in and out of dispersion, such as paramagnetic particles, reactions should readily be amendable to flexible automation using available lab automation solutions or dedicated micro-fluidic principles and enable significant reduction of probing volumes. The scalability and multiplexing capability opens up for the use of calibration curves, normalization to house-keeping proteins and internal standards to enable the generation of more accurate and quantitative data. Reactions on particles should also enable highly improved kinetics which in turn can be transferred to reduced analysis times.

The stipulated stabilizing effect of immobilizing proteins on particles is anticipated to enable further benefits in protein analysis workflows. The basic concept of the invention can be used as a means to generate pre-constructed calibration bead-sets that can be used in conjunction with the method for protein analysis described above. Such calibration bead sets have a potential for improved stability over time compared to proteins in solution due to the fact that individual protein molecules are stably bound in an isolated state minimizing the likelihood of protein aggregation/precipitation. Further, the stable immobilization on the beads enables the use of storage solutions reducing other protein degradation routes. This effect could also be used to store immobilized proteins from a sample between sample acquisition and analysis. For example to enable de-coupling of sample acquisition and analysis, simplify distribution of samples between labs or to generate "ready-to-analyse" bio-banks.

In one preferred implementation of the nucleic detection step, Q-PCR is used. In another preferred implementation of the nucleic acid detection step, quantitative nucleic acid arrays are used. In a third preferred implementation of the nucleic acid detection step, sequencing implementations allowing counting individual sequence reads are used. In a fourth preferred implementation of the nucleic acid detection step, rolling circle products are detected using digital enumeration in a flow system or read-out using magnetoreflexometry.

EXPERIMENTAL SECTION

Example 1: Binding of Complex Protein Samples to NHS Activated Paramagnetic Beads in the Presence of SDS Experimental Sample Preparation Total protein from sonicated clarified Vero cells, was used for the investigation. Samples containing 1 mg/ml protein and 0-0.5% SDS in 150 mM triethanolamine, 500 mM sodium chloride, pH 8.3 were prepared. The samples containing SDS were heated at 95° C. for 5 minutes prior to coupling.

Coupling to NHS MagSepharose

32 µl NHS MagSepharose beads (i.e. 160 µl of 20% slurry, GEHC Bio-Sciences AB) were equilibrated with 1 mM HCl and incubated with 32 µl sample with slow end-over-end mixing for 20 min at room temperature. The sample was removed and analyzed by SDS-PAGE [11] (reducing conditions) using Deep Purple Total Protein Stain (fluorescence) and imaging with Ettan DIGE imager (GEHC Bio-Sciences AB).

Results and Discussion

Figure 3:
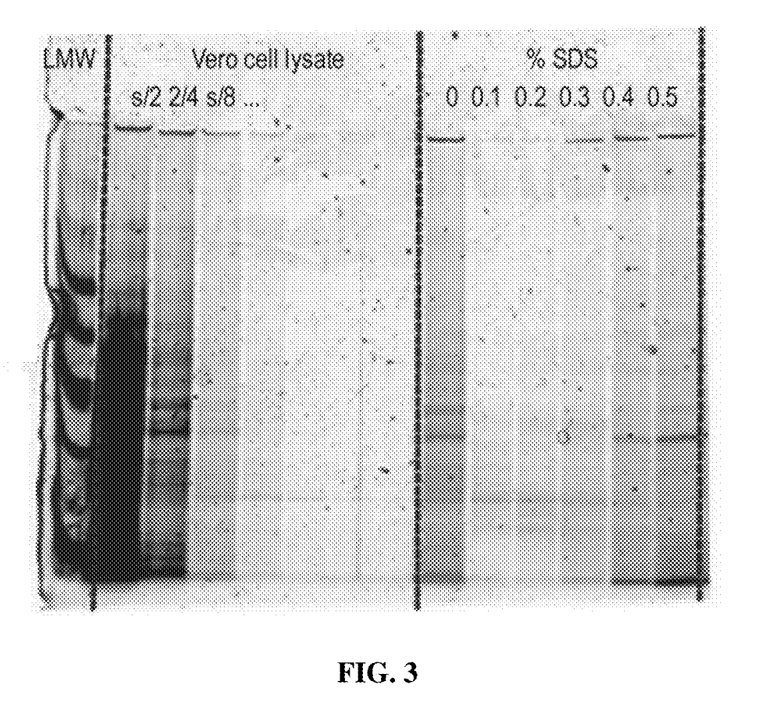
FIG. 3 SDS-PAGE gel image data showing feasibility of coupling a broad repertoire of proteins from denatured complex protein samples in the presence of different amounts of SDS to NHS activated paramagnetic beads. Left panel represents the amount and distribution of proteins in different dilutions of the original Vero cell lysate sample. Note that the sample is diluted 1+1 when applied to the beads, i.e. lane S/2 corresponds to 0% coupling efficiency. The right panel represents the amount and distribution of proteins remaining in the supernatant following 5 min treatment at 95° C. (For SDS containing samples) and incubation with NHS activated beads.

To investigate how efficiently a complex protein mixture can be coupled to magnetic beads after treatment with SDS at 95° C., total protein from a Vero cell lysate was coupled on NHS MagSepharose after treatment with 0.1-0.5% SDS at 95° C. for 5 minutes and without SDS and heat treatment as a reference. Coupling efficiency was investigated by SDS-PAGE of protein remaining in the supernatant after coupling. The SDS-PAGE fluorescence image, see FIG. 3, showed that the coupling efficiency was around 80% using 0.1-0.3% SDS, i.e. coupling of proteins to NHS MagSepharose was not negatively impacted by the presence of moderate concentrations of SDS. At higher SDS concentrations, coupling efficiency was reduced but not dramatically up to 0.5% SDS. With heat denaturation and the protein to SDS ratios used, proteins should be denatured, elongated and be present in the form of protein-SDS complexes. The obtained results show that a large diversity of proteins does still contain primary amine groups that are accessible and capable of reacting with NHS groups on a solid phase. Further that the binding efficiency was not severely impacted by the proteins being present in elongated forms or by presence of competing low-molecular weight primary amines such as amino acids or glutathione in the cell lysate. The gel data indicates that a few proteins do bind less efficiently, however by implementing calibration curves this should not represent a major hurdle for the intended overall protein analysis workflow. In addition to feasibility for coupling to NHS activated porous paramagnetic beads, for those skilled in the art, the obtained results indicates general feasibility for binding of a broad population of proteins from SDS treated complex protein samples using approaches based on covalent coupling to activated and dispersible solid surface structures.

Example 2: Full Blotting Beads Assay Implementation Using Paramagnetic NHS Beads and Proximity Extension Assay Reactions Experimental Sample Preparation Transferrin (Calbiochem) was used as a target protein and was serial diluted in a Vero cell lysate made by sonication in PBS (Lonza). Final samples were conditioned with coupling buffer [12] prior to coupling to beads and contained transferrin concentrations in the range of 0.001 ng/ml to 10000 ng/ml in 100 µg/ml total cell lysate, either without SDS or including 0.1% SDS (Merck). Samples for full workflow implementation were first incubated with 2% SDS for 5 min at 95° C. (at 20× the above protein concentrations) before being 20-fold diluted in coupling buffer [12].

Blotting Beads Assay

Polyclonal anti-transferrin antibody (GEHC, internal) was split into two aliquots and conjugated to either probe A or probe B (Olink Bioscience, www.olink.com) according to the manufacturer protocol [13]. NHS MagSepharose beads (10 µl of 20% slurry, GEHC) were equilibrated with 1 mM HCl and incubated with the samples (50 µl) with slow mixing for 40 min at RT. The beads were washed according to the NHS MagSepharose manual [12], then with PBS and finally Calibrator Diluent was added (10 or 20 µl, Olink Bioscience, www.olink.com). Proximity extension assay (PEA) was performed according to the manufacturer protocol [13], however with the proteins attached on the NHS MagSepharose. Hence, only 1 µl bead slurry solution (20% slurry) from the protein coupling/display step (5-10% of total population) was transferred to antibody/PEA-probe incubation step. Further, only 4 µl of a total volume of 100 µl after proximity extension reactions were transferred to the Q-PCR step for detection (0.2-0.4% overall workflow transfer efficiency).

Results and Discussion

Figure 4:
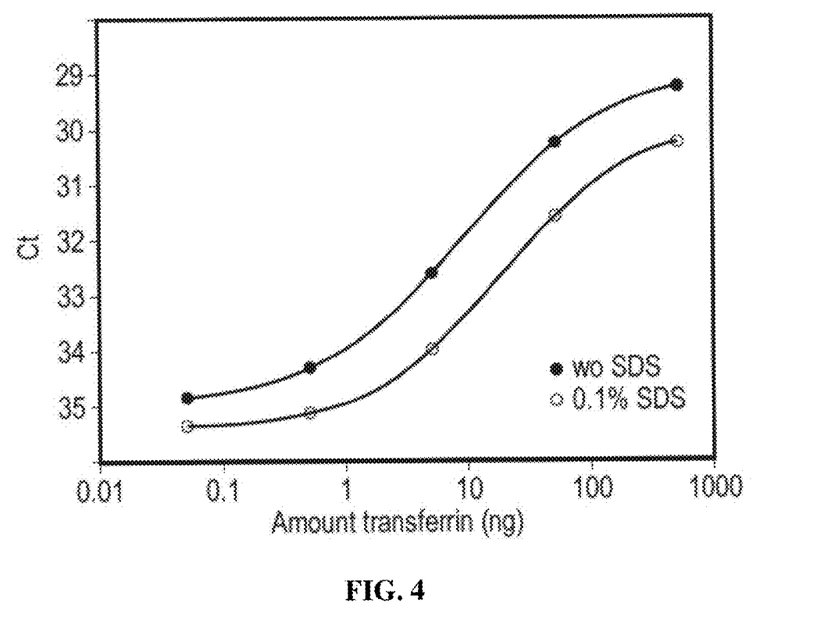
FIG. 4 Q-PCR calibration curve data showing feasibility of (i) Achieving successful PEA reactions on proteins coupled to porous paramagnetic NHS beads in the presence of moderate amounts of SDS (ii) Being able to detect and quantify a specific protein at low amounts and with a complex background of other proteins in excess using a non-specific first capture step. Transferrin was spiked at different amounts into a 0.1 mg/ml Vero cell lysate. The x-axis represents the total amount of transferrin present in the bead coupling step for different samples.

In order to investigate if the PEA procedure [13] could be performed and yield a quantitative response for proteins non-specifically captured to porous paramagnetic beads, known concentrations of target protein (transferrin) spiked in Vero cell lysate were coupled to NHS MagSepharose prior to analysis by PEA. Transferrin (0.05 to 500 ng) was specifically detected in cell lysate (100 µg/ml), with linear response of 2 logs between 1-100 ng, as shown in FIG. 4. Negative controls investigating PEA with either Vero cell lysate without transferrin spiked in or beads only gave low responses at background level (data not shown). An important conclusion from this result is that it shows the feasibility of a key aspect of the new methodology: detecting a specific protein in the presence of a large excess of a complex protein background using a non-specific solid phase capture step (Transferrin to background protein ratios of $10^{-4}$-$10^{-5}$ at LoD). As expected from the results in Example 1, coupling of proteins to NHS MagSepharose was not influenced by the presence of moderate concentrations of SDS. FIG. 4 show that diluting transferrin in Vero cell lysate containing 0.1% SDS at coupling to the beads did not have a direct negative influence on PEA either. The shift in Ct level between 0.1% SDS and absence of SDS can partly be attributed to (a) a difference in mass transfer; 0.1% SDS experiment had a 0.2% transfer rate compared to 0.4% non-SDS samples and (b) samples were from different transferrin dilutions.

Figure 5:
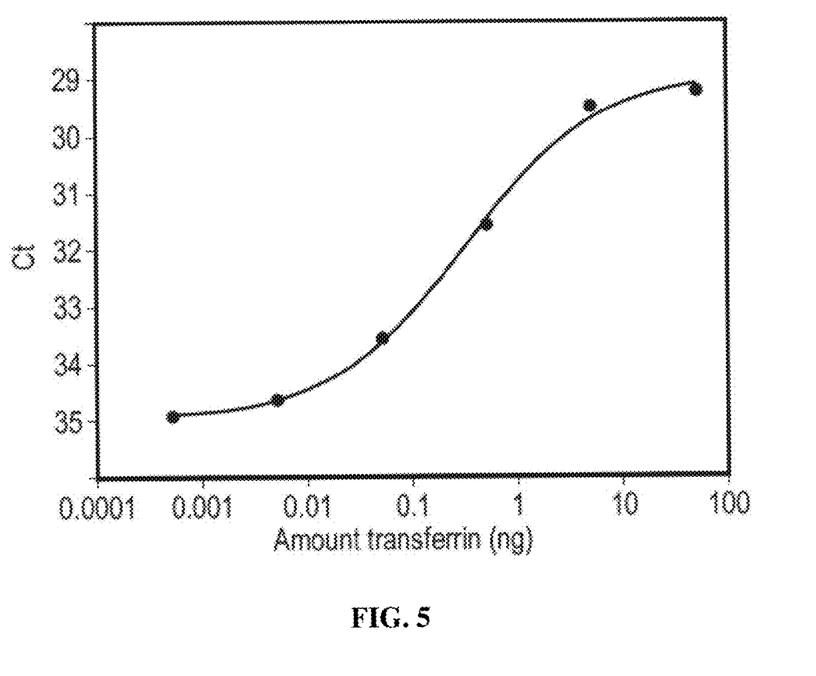
FIG. 5 Q-PCR calibration curve data showing feasibility of the full concept as described in FIG. 2. Vero cell lysate samples (2 mg/ml protein) with different amounts of spiked transferrin and 2% SDS were incubated for 5 min at 95° C., then diluted 20-fold before going through the steps described in FIG. 2. The x-axis represents the total amount of transferrin present in the bead coupling step for different samples.

In the intended final implementation of the Blotting beads assay, protein extraction would include harsh denaturing conditions. To evaluate if the Blotting Beads principle is compatible with such harsh conditions, transferrin dilutions in Vero cell lysate (2000 µg/ml) were pre-treated with 2% SDS and incubated at 95° C. for 5 min. Following this treatment most proteins should be fully denatured and forming complexes with SDS. Before coupling to beads, samples were diluted 20× in coupling buffer, yielding an SDS concentration at ~0.1% SDS. This is an SDS concentration that should be able to maintain proteins in solution. The pretreatment did not influence the PEA assay negatively. The assay shows a limit of detection of 0.2 pg transferrin and a dynamic range of around $10^5$ (Transferrin to background protein at LoD ~$10^{-7}$), see FIG. 5. In addition to the feasibility of coupling denatured proteins in the presence of SDS already shown in Example 1, these results show the feasibility of enabling epitope presentation compatible with specific affinity reagent detection without variable losses due to protein precipitation during SDS removal. Further, they show that a polyclonal antibody preparation can be used with the Blotting Beads assay principle to yield high specificity protein detection in a complex protein sample. The obtained results are highly competitive compared to state-of-the-art Western Blot implementations that typically can reach a LoD of ~10 pg and a dynamic range of around $10^2$. Further, the Blotting Beads assay has potential for substantial further basic performance improvements by e.g. taking advantage of the paramagnetic beads to (a) optimize workflow transfer in the assay (250-fold performance improvement potential) and (b) enable highly increased antibody/PEA probe concentrations without background signal increases. As 92-plex PEA assays for solution samples are available (Olink Bioscience, www.olink.com), the specific implementation can likely be extended to enable detection of many proteins in parallel (multiplexing).

In addition to showing feasibility for a specific implementation of the Blotting Beads concept, for those skilled in the art, the obtained results indicate feasibility for the more general principles of the concept: Different implementations combining covalent coupling of proteins based on broad protein specificities, to different types of populations of discrete and dispersible structures (e.g. micro-particles, nano-particles, nano-fibers or combinations thereof) and utilizing affinity assays with two or more specificity building steps to generate protein specific nucleic acid signals that can be detected and quantified using a suitable sequence specific nucleic acid detection method.

Example 3: Feasibility of Blotting Beads Assay Implementation Using NHS Based Biotinylation and Binding to Paramagnetic Beads with Streptavidin Ligands Biotinylation Sample Preparation All protein samples (GFP-His, transferrin, Vero cell lysate) were biotinylated using EZ-Sulfo-NHS-LC-Biotin reagent (Thermo Scientific, art. no. 21217) according to the manufacturer. For tests with GFP-His a recombinant histidine-tagged Green Fluorescent Protein) 21 mg/ml (745 µM) in pH 7.4 was used without or in the presence of 3% SDS (0.5% SDS and 7.4 mg/ml protein in actual biotinylation reaction).

Estimation of Biotinylation Degree

Residual excess of the biotinylation reagent in the GFP-His samples was removed by purification of the histidine-tagged proteins by IMAC (Immobilized Metal-ion Affinity Chromatography) using His MagSepharose Ni magnetic beads (GEHC, art. no. 28-9673-88). Sample load was about 14.8 mg GFP-His/ml beads. Samples were incubated for 15 minutes at room temperature. The beads were then washed two times with PBS or PBS+0.1% SDS (for samples with and without SDS respectively). Bound proteins were eluted with 500 mM imidazole or 500 mM imidazole+0.1% SDS. The eluates were analyzed for biotin and protein content.

Results

Biotin content in respective GFP-His sample eluted from His MagSepharose Ni beads was measured using a HABA/Avidin assay [14]. Protein concentration was estimated by measuring the absorbance at 280 nm. The average amount of biotin incorporated into GFP-His was calculated to 2.8 biotin/GFP-His in the sample lacking SDS during the biotinylation reaction. Total protein recovery was 81%. The average amount of biotin incorporated into GFP-His in the sample containing SDS during the biotinylation reaction was calculated to 4.6 biotin/GFP-His. Total protein recovery was 76%.

Binding to Streptavidin Beads

Experimental

Biotinylated BSA (Sigma, art. no. A8549) was used as model protein. Four different concentrations of SDS were tested, 0.01, 0.1, 0.7 and 1.0%. The effect of 6 or 0.6 M guanidinhydrochloride on streptavidin binding was also studied. An amount of 100 µg protein was incubated with 10 µl streptavidin MagSepharose beads (GEHC, art. no. 28-9857-99) in a total volume of 300 µl for 30 min. 200 µl of the supernatants were transferred to a 96-well plate and the absorbance at 280 nm was determined using a plate reader. The differences between the determined unbound biotin-BSA in the supernatant and the amount biotin-BSA added to the assay were considered to represent streptavidin bound biotinylated protein.

Results

Figure 6:
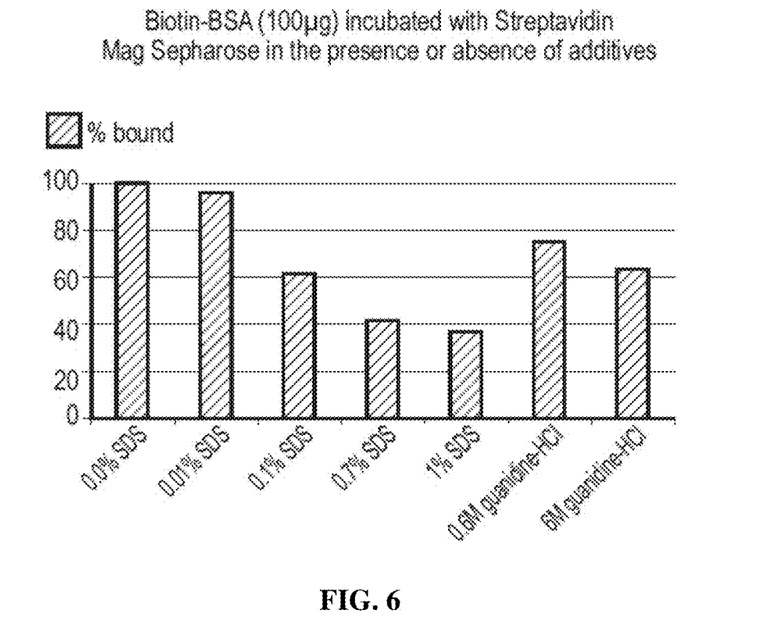
FIG. 6 Graph showing binding efficiencies of biotinylated protein to streptavidin beads in the presence of SDS and other additives. Binding efficiencies are normalized to percentage of binding as compared to samples lacking additives.

The results from the studies are summarized in FIG. 6. Calculation was done on the separate experiments using respective sample without SDS as reference (100% binding). A blank for each separate buffer was used in the calculations. As can be seen binding to streptavidin beads occurs even at 1% SDS but is reduced steadily with increased amounts of SDS.

PEA Assay on Streptavidin Beads

Sample Preparation

Biotinylated Vero cell lysate (1 mg/ml) was diluted in PBS to 1 ml 50 µg/ml. Biotinylated transferrin was mixed with biotinylated cell lysate to final concentrations of 100 µg/ml biotinylated transferrin and 50 µg/ml cell lysate and was then diluted in cell lysate in 10× dilution-series from 10000 ng/ml to 0.001 ng/ml.

Binding of Samples to Streptavidin Functionalized Beads

Streptavidin MagSepharose beads, 10 µl of 10% slurry, (GEHC, art. no. 28-9857-99) were washed with PBS and incubated with 50 µl of the biotinylated transferrin in cell lysate dilutions for 2 h at room temperature on shaking. The beads were then washed with PBS and 10 µl Calibrator Diluent was added. Transferrin concentration were then analyzed by PEA (Proseek Assay development kit, Olink Bioscience, art. no. 93101-0100) according to the manufacturer protocol [13], however with the proteins attached on the streptavidin MagSepharose beads. Hence, only 1 µl bead slurry solution (10% slurry) from the protein coupling/display step (10% of total population) was transferred to antibody/PEA-probe incubation step. Further, only 4 µl of a total volume of 100 µl after proximity extension reactions were transferred to the Q-PCR step for detection (0.4% overall workflow transfer efficiency).

Results

Figure 7:
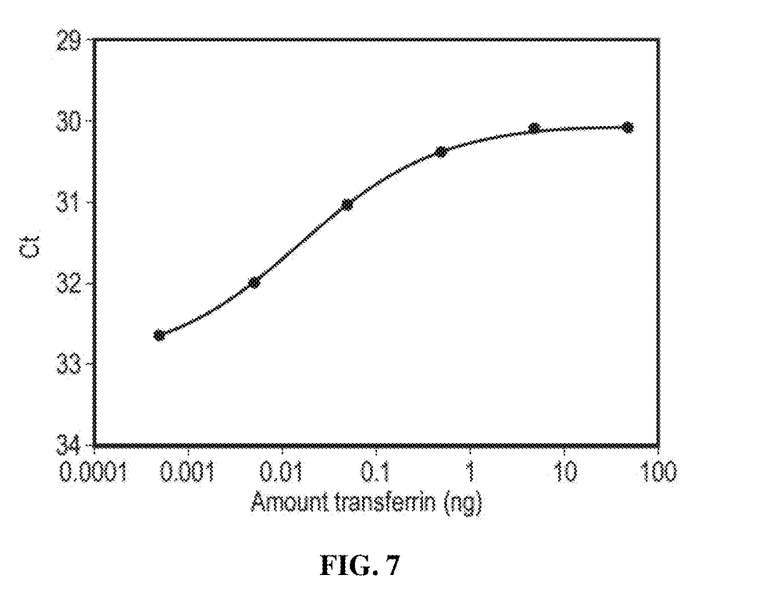
FIG. 7 Q-PCR calibration curve data showing feasibility of detecting and quantifying a specific biotinylated protein in the presence of an excess complex background of biotinylated proteins by displaying the proteins on porous paramagnetic streptavidin beads, performing PEA reactions on the beads and using Q-PCR read-out. Biotinylated transferrin was spiked at different concentrations into a 0.1 mg/ml biotinylated Vero cell lysate. The x-axis represents the total amount of transferrin present in the streptavidin bead coupling step for different samples.

FIG. 7 shows transferrin at the various concentrations analyzed by PEA. As can be seen a limit of detection around 1 pg transferrin and a dynamic range of around $10^4$ could be achieved.

Overall Discussion

The results show that biotinylation via NHS coupling can be achieved using denaturing conditions and in the presence of high amounts of SDS (0.5%). The general compatibility with coupling using harsh SDS conditions is also further evidenced by the results obtained in Example 1. Further, it is shown that even high amounts of SDS does not disrupt the biotin-binding capacity of streptavidin ligands and that high binding levels can still be achieved. Finally, detection of a specific protein in the presence of a large excess of other proteins (ratios of $<10^{-5}$ can be achieved also using the general biotin/streptavidin display principle and by applying PEA on porous paramagnetic streptavidin beads. Together with the results in Example 2 these results indicate the feasibility of implementing the full Blotting Beads concept using an initial biotinylation step followed by display on streptavidin beads and PEA read-out. For those skilled in the art it is understood that alternative implementations should also be feasible: e.g. implementations based on other combinations of hapten based conjugation reagents, various structures (micro-particles, nano-particles, nano-fibers or combinations thereof) having ligands forming strong and specific bounds with said hapten and utilizing affinity assays with two or more specificity building steps to generate protein specific nucleic acid signals that can be detected and quantified using a suitable sequence specific nucleic acid detection method.

REFERENCES

[1] Michael A Gillette & Steven A Carr, Quantitative analysis of peptides and proteins in biomedicine by targeted mass spectrometry, |VOL. 10 NO. 1|JANUARY 2013|nature methods

[2] I. Weibrecht et al., Proximity ligation assays: a recent addition to the proteomics toolbox, Expert Rev. Proteomics 7(3), 401-409 (2010)

[3] M. Lundberg et al., Homogeneous antibody-based proximity extension assays provide sensitive and specific detection of low-abundant proteins in human blood, Nucleic Acids Research, 2011, 1-8 doi:10.1093/nar/gkr424

[4] J. Goransson et al., Rapid Identification of Bio-Molecules Applied for Detection of Biosecurity Agents Using Rolling Circle Amplification, PlosOne|February 2012|Volume 7|Issue 2|

[5] Unfolding proximity probes and methods for the use thereof, patent application WO 2012/152942 A1

[6] T. Zardan Gomez et al., Detection of rolling circle amplified DNA molecules using probe-tagged magnetic nanobeads in a portable AC susceptometer, Biosensors and Bioelectronics 29 (2011) 195-199

[7] S. Darmanis et al., ProteinSeq: High-Performance Proteomic Analyses by Proximity Ligation and Next Generation Sequencing, PlosOne|September 2011|Volume 6|Issue 9|

[8] Y. Liu et al, Western blotting via proximity ligation for high performance protein analysis, Mol Cell Proteomics. 2011 November; 10(11)

[9] PROXIMITY LIGATION TECHNOLOGY FOR WESTERN BLOT APPLICATIONS, patent application number WO2012057689A1

[10] L. Gold et al., Aptamer-based multiplexed proteomic technology for biomarker discovery, PLoS One. 2010 Dec. 7; 5(12)

[11] Instructions for ExcelGel SDS, gradient 8-18, GE Healthcare 80-1310-00.

[12] Instruction manual NHS Mag Sepharose™ 28-9537-64, GE Healthcare AB.

[13] Users manual Proseek® Assay Development kit, Olink Bioscience.

[14] Green, N. M.; A spectrophotometric assay for avidin and biotin based on binding of dyes by avidin. Biochem. J., 1965, 94, 23c-24c.

The invention claimed is:

1. A method for protein analysis comprising providing a denatured protein sample in the presence of a denaturing agent, the method comprising the following steps;
   a) contacting said denatured protein sample with a population of protein-binding structures to capture a plurality of different proteins on said structures, wherein said structures are discrete and dispersible,
   b) removing the denaturing agent to display protein- and protein-feature specific epitopes from said sample on said structures;
   c) performing affinity probing targeted to a sub-group of said protein or protein feature specific epitopes requiring two or more specificity building events per targeted protein or protein feature with affinity probes comprising an oligonucleotide, thereby resulting in a target specific nucleic acid molecule or sequence for each of the targeted proteins or protein-features;
   d) liberating said protein- or protein-feature specific nucleic acid sequences from said structures;
   e) optionally amplifying said nucleic acid sequences;
   f) analysing the nucleic acid molecules by a quantitative and sequence specific nucleic acid detection method; and
   g) determining therefrom the quantity or presence of targeted proteins or protein features in said sample.

2. The method according to claim 1, wherein the protein binding structures are selected from the groups of microparticles, nanoparticles, nanofibers, and combinations thereof.

3. The method according to claim 2, wherein the protein binding structures are selected from porous or non-porous structures of natural or synthetic polymers, ceramic structures, metallic structures, and combinations thereof.

4. The method according to claim 3, wherein the protein binding structure is a paramagnetic agarose bead.

5. The method according to claim 1, wherein the protein binding structures in the population all have identical binding specificities.

6. The method according to claim 1, wherein the protein binding structures collectively have multiple binding specificities.

7. The method according to claim 6, wherein multiple proteins or protein features are targeted by affinity probing and nucleic acid detection to generate a multiplex determination of quantity or presence of said proteins or protein features simultaneously.

8. The method according to claim 7, wherein the proteins in said denatured protein sample have been conjugated to a hapten and said protein binding structures contain an affinity ligand directed against the hapten.

9. The method according to claim 8, wherein the hapten is biotin and the affinity ligand is streptavidin or avidin.

10. The method according to claim 9, wherein unreacted excess hapten reagents are reduced or removed following conjugation and prior to contacting the sample with protein binding structures.

11. The method according to claim 1, wherein said protein binding structures are chemically activated and contacting said sample results in covalent coupling of proteins to the structures.

12. The method according to claim 11, wherein said protein binding structures are NHS activated.

13. The method according to claim 1, wherein the protein denaturing agent is selected from the group consisting of sodium dodecyl sulfate, lithium dodecyl sulfate, Urea, Thio-Urea, and Guanidine-HCl.

14. The method according to claim 13, wherein the provided denatured protein sample resulted from heating a protein sample to above 80° C. in the presence of a denaturing agent from said group.

15. The method according to claim 13, wherein the SDS concentration in said sample is reduced to a range of 0.1-0.3% prior to step a) contacting the denatured protein sample with protein binding structures, wherein the method further comprises the steps of:
   (i) contacting the denatured protein sample with porous lid beads designed with a hydrophilic surface layer allowing only low molecular weight molecules to enter the inner pore volume which is modified with octylamine ligands having affinity for SDS;
   (ii) allowing SDS to accumulate within the lid beads for a defined time period; and
   (iii) removing the lid beads from the denatured protein sample of step (i).

16. The method according to claim 1, further comprising the steps of:
   (i) following capture on the protein binding structures in step a),
   (ii) the population of structures are isolated and re-suspended in a stability promoting storage solution,
   (iii) and before b) and c) the structures are isolated from the storage solution and re-suspended in a buffer suitable for affinity probing.

17. The method according to claim 1, wherein the affinity probing comprises the following steps:
   (i) contacting the structures with captured proteins with one or multiple aptamers each having been selected for having high affinity and slow-off rate for a single protein- or protein feature specific epitope;
   (ii) isolating the structures after having allowed time for protein-aptamer binding;
   (iii) re-suspending the structures in a solution containing poly-anions to promote a differential release of non-specifically bound aptamers enabled by the slow off-rate of the specific interaction;
   (iv) isolating the structures; and
   (v) re-suspending the structures in a solution and treating them to promote elution of the aptamers still bound after the poly-anion treatment.

18. The method according to claim 1, wherein the affinity probing employs affinity binders coupled to oligonucleotides and results in target specific nucleic acid molecules as a result of a combination of proximal binding of two or more affinity binders carrying different oligonucleotides to the same protein or protein-feature target and the action of nucleic acid processing enzymes added during the probing.

19. The method according to claim 18, further comprising the steps of:
 (i) using rolling circle amplification reactions to create DNA-spheres consisting of condensed linear repeats of protein or protein feature specific nucleic acid molecules;
 (ii) hybridizing the DNA spheres with labelled detection oligonucleotides specific for each protein or protein feature specific DNA sphere; and
 (iii) detecting a signal proportional to the number of DNA spheres present.

20. The method according to claim 19, wherein the DNA spheres are fluorescently labelled and digitally counted in a flow system.

21. The method according to claim 19, wherein the DNA spheres are labelled by magnetic nanoparticles and detected using magnetorelaxometry.

22. The method according to claim 18, wherein the affinity probing employs proximity extension reactions or proximity ligation reactions.

23. The method according to claim 1, wherein quantitative PCR, an oligonucleotide array or a sequencing procedure allowing counting individual sequence readings is used as the nucleic acid detection method.

* * * * *